United States Patent [19]
Lu et al.

[11] Patent Number: 5,443,985
[45] Date of Patent: Aug. 22, 1995

[54] CELL CULTURE BIOREACTOR

[75] Inventors: George Z. Lu; Murray R. Gray; Bradley G. Thompson, all of Edmonton, Canada

[73] Assignees: Alberta Research Council; The Governors of the University of Alaska, both of Edmonton, Canada

[21] Appl. No.: 95,681

[22] Filed: Jul. 22, 1993

[51] Int. Cl.[6] ............ C12N 5/02; C12M 3/02
[52] U.S. Cl. ............ 435/240.25; 435/240.24; 435/286; 435/313
[58] Field of Search ............ 435/240.1, 240.2, 240.22, 435/240.23, 240.24, 240.25, 284, 286, 311, 314, 313, 315, 316, 812, 813, 818; 261/77, 121.1, 123

[56] References Cited

U.S. PATENT DOCUMENTS

| | | | |
|---|---|---|---|
| 1,019,003 | 2/1912 | Aminoff | 261/123 |
| 1,983,058 | 12/1934 | Wait | 261/123 |
| 3,402,103 | 9/1968 | Amberg et al. | |
| 3,506,541 | 4/1970 | Snelling | 261/123 |
| 3,575,813 | 4/1971 | Rothmayr | |
| 4,228,242 | 10/1980 | Girard et al. | 435/284 |
| 4,343,904 | 8/1982 | Birch et al. | 435/285 |
| 4,649,117 | 3/1987 | Famiuetti | 435/313 |
| 4,898,718 | 2/1990 | Cardoso | 422/211 |
| 4,906,577 | 3/1990 | Armstrong et al. | 435/313 |
| 5,057,428 | 10/1991 | Mizutani et al. | 435/285 |
| 5,057,429 | 10/1991 | Watanabe et al. | 435/286 |

FOREIGN PATENT DOCUMENTS

| | | | |
|---|---|---|---|
| 0164888 | 12/1985 | European Pat. Off. | 435/286 |
| 0343885 | 11/1989 | European Pat. Off. | 435/313 |
| 58-134989 | 8/1983 | Japan | |
| 60-251878 | 5/1984 | Japan | |
| 0075273 | 4/1985 | Japan | 435/287 |
| 62-118878 | 11/1985 | Japan | |
| 62-044173 | 2/1987 | Japan | |
| 2044173 | 2/1987 | Japan | 435/312 |
| 3164879 | 7/1988 | Japan | 435/286 |
| 1097669 | 1/1968 | United Kingdom | |
| 2202549 | 9/1988 | United Kingdom | 435/313 |
| 0372253 | 3/1973 | U.S.S.R. | 435/287 |
| 8901029 | 2/1989 | WIPO | 435/286 |

*Primary Examiner*—William H. Beisner
*Attorney, Agent, or Firm*—Finnegan, Henderson, Farabow, Garrett & Dunner

[57] ABSTRACT

The invention provides a bioreactor for culturing living cells, particularly shear sensitive cells, wherein the bioreactor is composed of a stationary vessel with opposite spaced walls inclined at an angle to form upper and lower walls. Liquid culture medium and cell culture, such as hybridoma cells, are introduced into the vessel and gas is introduced at the lower end of the vessel to form gas bubbles which travel upward along the upper wall of the bioreactor to disengage from a small portion of the gas liquid interface. The gas bubbles circulate the cells and liquid medium, maintaining the cells in suspension and lifting them in a circulating path upwardly parallel to the upper wall and downward along the lower wall. The bioreactor design thus achieves bulk mixing and aeration by maintaining a significant degree of segregation between the upwardly travelling bubbles and the cells in the liquid medium avoiding unnecessary cell damage by fluid-mechanical shear or by bubble bursting events.

16 Claims, 3 Drawing Sheets

CELL CULTURE BIOREACTOR

FIELD OF THE INVENTION

The invention relates to a bioreactor and method for culturing cells, particularly shear sensitive cells.

BACKGROUND OF THE INVENTION

Many cell lines are very sensitive to fluid-mechanical stresses such as shear forces. Generally, animal cells, insect and plant cells are difficult to culture on a large scale due to shear sensitivity. Bioreactors for shear sensitive cells must provide gentle agitation so as to minimize shear, while still providing sufficient mixing and aeration for growth. The balance is difficult to maintain.

Conventional airlift bioreactors typically include a concentrically placed draft tube within the bioreactor vessel. Air is introduced at the base of the reactor, creating a density difference in the liquid medium. The rising bubbles provide oxygen for growth and circulate the cells and liquid medium by airlift. Such bioreactors tend to cause strong fluid shear force detrimental to growth and productivity for shear sensitive cells. The bubbles may coalesce into larger bubbles as they rise, and upon contacting the surface, the bursting bubbles create extreme shear stress on the cells (bubble shear) leading to metabolic stress or cell destruction.

Classical stirred tank bioreactors provide aeration through a sparger, pipe or perforated ring at the bottom of the reactor vessel. Agitation is accomplished by impellers such as flat plates, helical blades or a screw type auger mounted on a central rotating shaft. Such means of agitation and aeration generally cause turbulent flow characteristics resulting in fluid-mechanical shear stress to shear sensitive cells.

Several bioreactors have been designed specifically for shear sensitive cells. For instance, U.S. Pat. No. 4,906,577 issued May 6, 1990 to Armstrong et al. discloses a bioreactor having a lower stirred cell culture tank and an upper compensation chamber so as to operate with zero head space. A gas exchange tube is located in the culture tank to cause an outer downflow zone and a central upflow zone. A screw type auger stirrer is centrally located in the tank.

U.S. Pat. No. 4,649,117 issued Mar. 10, 1987 to Familletti et al. provides a bioreactor having two chambers, an upper wider chamber and a lower, smaller diameter chamber connected by inwardly sloping side walls. Agitation is accomplished by introducing a gently flowing gas stream centrally at the base of the lower chamber.

The above reactors suffer several disadvantages, including complexity of design and/or undesirable levels of cell damage due to fluid-mechanical shear or bubble bursting.

Several inclined bioreactor designs have been proposed in the past. Japanese Patent 58-134989 discloses a rotatable cylindrical culture tank. The tank is rotated about its horizontal axis and gas is sparged through a horizontal pipe at the bottom of the tank. The tank may be inclined at an angle less than 45° from the horizontal. An angle greater than 45° is stated to cause settling problems which necessitate rotation at a too high of a rate.

Japanese Patent 62-44173 discloses a similar rotatable cylindrical bioreactor. The axis is inclined at 5–55 degrees from the horizontal. The reactor is rotated along its axis to cause a gradient in the distribution of adhesion dependent and floating type cells.

U.S. Pat. No. 5,057,429 issued Oct. 15, 1991 to Watanabe et al. discloses a cell culture apparatus wherein the cells and culture media are contained in a semipermeable bag which is rotated or shaken at various angles.

Agitation in the above reactors is achieved by partial rotation, shaking or rotation tumbling, all of which cause unacceptable levels of mechanical shear and bubble shear, as discussed hereinabove. Furthermore, the bioreactor design is complicated by the need to provide complex means for rotation together with seals for gas inlets and shafts into a rotating vessel.

SUMMARY OF THE INVENTION

The inventors discovered that the fluid-mechanical and bubble bursting shear damage imparted to shear sensitive cells can be minimized, without compromising aeration, by altering the design of the bioreactor so as to minimize contact between the cells and gas bubbles. The bioreactor of this invention includes inclined, preferably parallel walls, with air or other circulating gas being introduced at the base of the reactor. The spaced apart walls may be the wall of an inclined cylindrical reactor or may be inclined, spaced apart plates. In the bioreactor of this invention, cell damage is minimized by segregating the cells from the upwardly travelling bubbles. The bubbles and liquid medium are circulated upwardly along the upper inclined wall of the reactor. The bubbles disengage only from a very small portion of the gas-liquid interface, while the cells and liquid growth medium are circulated downwardly, by gravity, along the lower inclined wall of the bioreactor. Sufficient aeration and bulk mixing is achieved with the bioreactor design, without imparting unnecessary cell damage by fluid-mechanical shear or by bubble bursting events.

Broadly stated, the invention provides a bioreactor for cultivating living cells in a liquid culture medium. The reactor includes a stationary vessel enclosing the cells and liquid medium, the vessel having oppositely spaced walls. The walls are inclined at an angle from the vertical so as to form an upper and a lower wall. The walls are tapered at their lower ends. Means for introducing a circulating gas is provided at the lower ends of the walls.

In another broad aspect, the invention provides a method of culturing living cells. The method comprises the steps of (a) providing a vessel having oppositely spaced walls inclined at an angle to the vertical so as to form an upper and a lower wall; (b) introducing a liquid culture medium and a cell culture to the vessel; and (c) introducing a gas at the lower end of the walls at a rate sufficient to circulate the cells and liquid medium, whereby the cells are maintained in suspension and are lifted in a recirculating path generally upwardly parallel to the upper wall and downwardly along the lower wall.

DESCRIPTION OF THE PREFERRED EMBODIMENT

Figure 1:
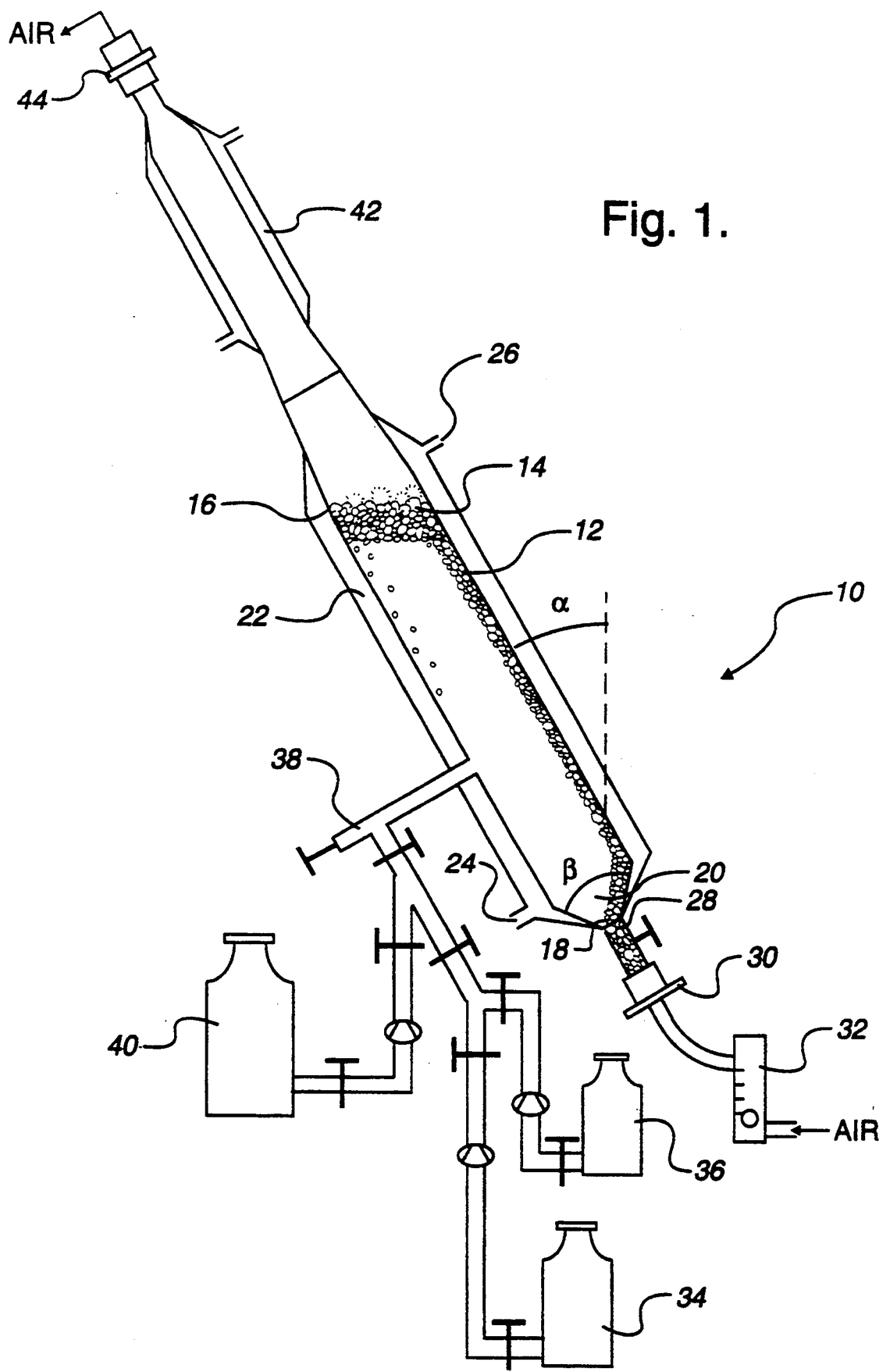
FIG. 1 is a schematic side sectional view of the bioreactor of this invention formed with an inclined cylindrical vessel.

Referring to FIG. 1, there is illustrated a bioreactor for use in culturing living cells, particularly shear sensitive cells, animal cells (including mammalian or other animal cells such as insect cells), plant cells and microbial cells. The bioreactor 10 includes a cylindrical culture vessel 12, inclined at an angle ($\alpha$) from the vertical. The vessel 12 may be made of any non-toxic biocompatible material such as PYREX ™ or stainless steel.

The vessel 12, being inclined, forms an upper wall 14 and a lower wall 16 which are preferably parallel to each other. The walls 14, 16 are tapered at their lower ends to an apex 18 of enclosed angle $\beta$, forming a conical section 20. The vessel 12 is surrounded by a heating jacket 22 to provide temperature control. Interior heating/cooling coils may alternatively be used. A heating fluid such as water is circulated through the heating jacket 22 through inlet and outlet ports 24, 26 respectively. For most cell culture, a temperature of about 37° C. is used.

A gas sparger 28 (such as sintered glass or metal) is located at the apex 18 of the conical section 20 for introducing a circulating gas such as air, $CO_2$, nitrogen, or mixtures thereof, into the bioreactor 10. The gas is introduced at a flow rate sufficient to suspend the cells to be cultured in a liquid culture medium and to circulate the cells and medium in a recirculating path, along the upper wall 14 and downwardly along the lower wall 16. A gentle gas flow rate is maintained to avoid shear stress or foaming problems. The flow rate will vary with the vessel dimensions, density of the reactor contents, oxygen needs of the cells and the angle of inclination. Typically, flow rates between about 0.01–0.05 vol.gas/vol.liquid/min are used. The gas is preferably introduced through an inlet gas filter 30 and a flowmeter 32.

The liquid culture and cell inoculum are introduced from supply containers 34, 36 respectively through an inlet and sampling port 38 located in the lower wall 16 of the vessel 12. An antifoam agent supply 40 may also be connected to inlet port 38 to limit foaming in the reactor.

Moisture control in the vessel 12 is preferably achieved by providing a water condenser 42 at the top of the vessel 12. Gases may be vented out the top of the condenser 42, through a filter 44. A small back pressure may be maintained on the vessel contents (which assists in maintaining sterile conditions in the vessel 12) by controlling the gas flow through filter 44.

Figure 2:
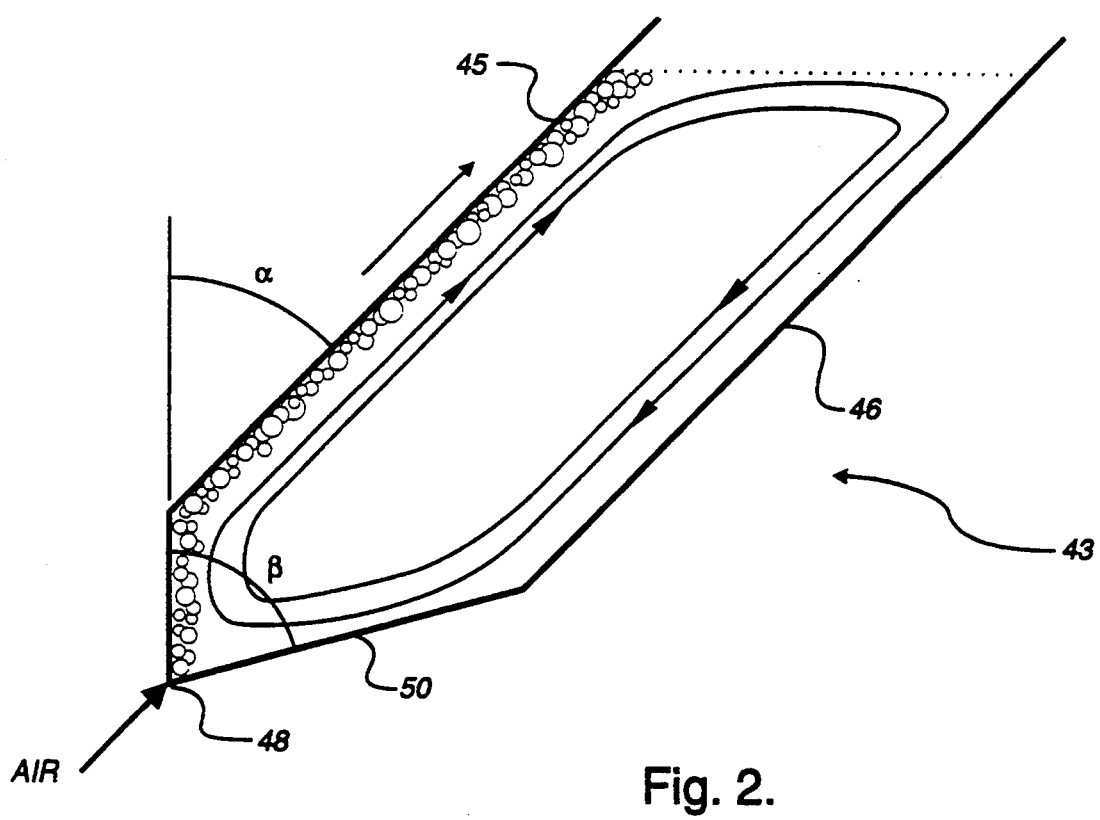
FIG. 2 is a schematic side sectional view of the bioreactor formed from inclined parallel spaced plates showing the approximate recirculating path of the cells and liquid medium.

In another embodiment, shown schematically in FIG. 2, the bioreactor 10 may be formed from a vessel 43 having upper and lower walls comprising inclined, spaced apart plates 45, 46, preferably parallel spaced. The plates 45, 46 are tapered to apex 48 at their lower ends to form a tapered section 50 (generally triangular in cross section). In scale up, the plates may be spaced further apart to increase reactor volume, or the plates 45, 46 may be stacked in series, with reactors being formed between each pair of plates. The plates 45, 46 are joined at their ends by end walls (not shown).

It should be understood that the conical and tapered sections 20, 50 of the vessels 12, 43 need not be shaped as shown in the Figures. For instance, sharp angles may be avoided with a generally hemispherical or curved shape. If the bioreactor 10 is formed from spaced plates 45, 46, the lower plate 46 may end short of length of the upper plate 45 and the lower plate alone may be tapered directly to the lower end of the upper plate 45. The terms "tapered", "conical section" and "tapered section", as used herein and in the claims are meant to include these and other design variations, any of which avoid formation of dead space at the base of the vessel 12, 43 where non-circulating cells or medium pockets may build up.

The angle of inclination ($\alpha$) of the upper and lower walls 14, 16 (or plates 45, 46) is preferably between about 10°–45° from the vertical. At inclination angles greater than about 45°, dead space may be created at the base of the bioreactor 10. At less than 10°, the benefit of decreasing the area over which the gas bubbles disengage from the surface is reduced.

The enclosed angle of the taper at the base of the reactor (the cone angle—$\beta$ in FIGS. 1 & 2) is preferably between 30°–80°, most preferably about 50°. A smaller cone angle can be used in any case, subject to ease of fabrication. A larger angle can give poor circulation of cells towards the lower end of the bioreactor at an inclination angle of 45°.

The flow pattern achieved by the bioreactor design of the present invention is shown schematically in FIG. 2. The liquid medium is lifted along the upper wall or plate 45 with the gas bubbles. The cells tend to fall toward the lower plate 46. However, as the air bubbles break the surface at the gas-liquid interface along the upper plate 45, the cells and liquid medium are pulled by gravity downwardly toward and along the lower wall or plate 46. This design reduces cell damage and destruction from bubble stress.

The bioreactor 10 is stationary, that is no rotation is needed for agitation or gas transfer. Gentle agitation is provided solely by the inclined reactor design and the introduction of the circulating gas at the base of the bioreactor 10. Mechanical agitators are not needed.

It is possible to operate the inclined bioreactor in a perfusion mode, wherein spent medium is withdrawn from the vessel 12 through a perfusion filter (not shown). The perfusion filter may advantageously be located along the upper wall 14, preferably toward the top of the upper wall but still below the liquid surface. This location minimizes plugging of the perfusion filter, a common problem with perfusion, since the filter is constantly swept by the liquid medium and gas bubbles, without a substantial number of cells since the cells fall downwardly toward the lower wall 16 near the top of the reactor.

The bioreactor 10 may also be operated with the use of microcarders or gel carders to which some shear sensitive cells adhere. Known microcarders include, without limitation, honey combed ceramic particles and thin or hollow fibre bundles. Gels include, without limitation, agar, agarose, carrageenin and gelatin. Whereas flotation of microcarriers and gels is a problem in conventional airlift reactors, flotation is minimized in the inclined bioreactor of the present invention due to the limited contact between the bubbles and microcarders and the downward settling of the microcarders.

The bioreactor 10 of this invention may be used with any types of living cells and tissues, whether naturally occurring, mutated, genetically engineered or hybrid cells. The cells may be grown in suspension, attached to a substrate, or attached microcarriers or gels. The term living cells, as used herein, is meant to include, in the foregoing forms, any animal cells, for example mammalian, amphibian, insect and foul, microbial cells, plant cells, algae cells and the like. Various liquid cell cultures are used, depending on the cells to be cultured. Standard media such as Basal Medium Eagles (BME), Eagle's Minimum Essential Medium (MEM), Dulbecco's Modified Eagle Medium and the like may be used. These culture media contain a carbohydrate source, essential amino acids, mineral salts and vitamins. They are frequently supplemented with mammalian sera such as fetal bovine serum (FBS).

The invention is further illustrated by the following non-limiting example.

EXAMPLE

Equipment

An inclined tube bioreactor as illustrated in FIG. 1 was constructed from clear Pyrex TM glass. The bioreactor had a working volume of about 4 L. A minimum working volume of 1.8 L was required due to the position of the sampling port (i.e. to cover the port).

The invention is not limited to specific dimensions but may be exemplified as follows: a cylindrical vessel 1000 mm long, 70 mm in diameter, a tapered conical section at the lower end 50 mm in length, the enclosed angle of which was 50°. The lower conical section tapered to a gas sparger of 25 mm in diameter. The angle of inclination of the vessel walls was 25° from the vertical.

Cell Line and Liquid Culture Medium

A murine hybridoma cell line secreting an antibody (IgG) reactive to human adenocarcinomas was cultivated in the inclined tube bioreactor. This cell line was known to be and is exemplary of other shear sensitive cells. Two vials stored in liquid nitrogen were thawed into culture medium with 10% fetal bovine serum (FBS) (obtained from Gibco, Grand Island, N.Y.) and were then subcultured for two weeks in the same medium. A master cell bank was then prepared for the experiments. The culture medium was prepared from RPMI-1640 (Gibco) supplemented with 1% glutamine (Gibco) and 5% FBS (Gibco). A 400 ppm amount of an antifoam agent (Antifoam C from Sigma Chemical Company, St. Louis, Mo.) was added into the medium in advance when starting a bioreactor run. To prepare the inoculum, a freezing vial from the master cell bank was thawed into the culture medium with 10% FBS. Two passages in culture medium with 10% FBS, followed by three passages in culture medium with 5% FBS were used. Two 500 mL spinners were used to prepare inoculum for the bioreactor cultures.

Cell Culture Experiments

Figure 3:
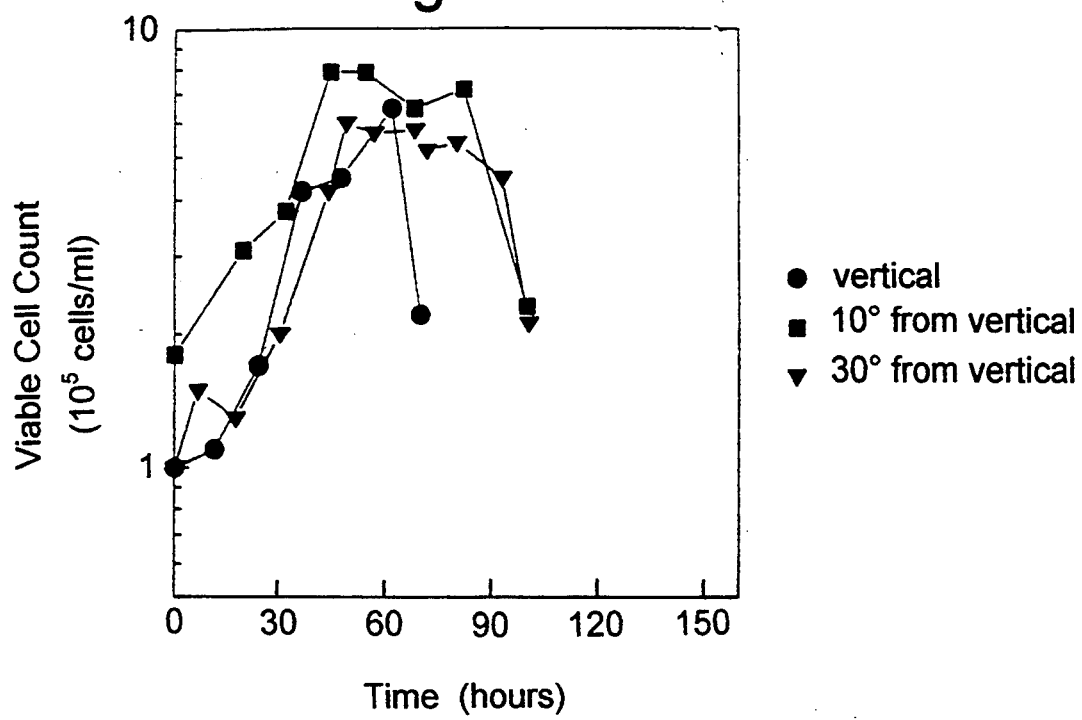
FIGS. 3 and 4 show two graphs plotting cell count and antibody production, respectively, against time for a shear sensitive murine hybridoma cell line cultured in a bioreactor disposed at different angles from the vertical (● 0° from vertical, ■ 10° from vertical and ▼ 30° from vertical).
Figure 4:
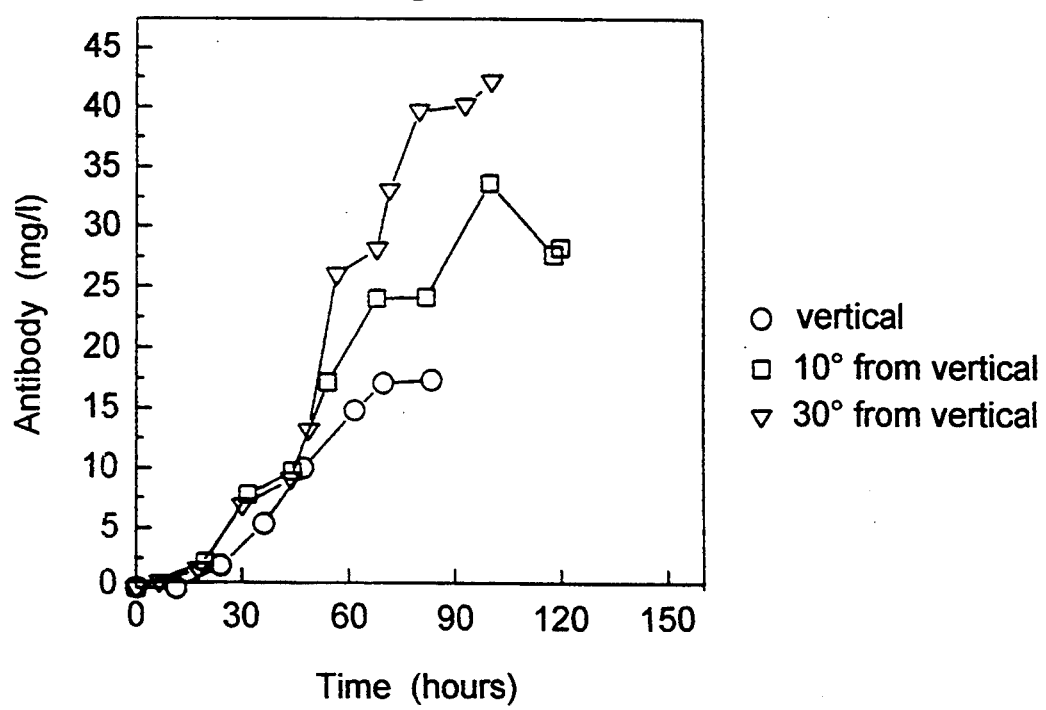

The water jacket of the bioreactor was maintained at 37° C. using a circulating water bath. Aeration of 0.05 vvm (volume of air per volume of liquid per minute) was provided by gas cylinders containing about 7% $CO_2$ in balanced air. The culture medium (2 L) with 5% FBS was pumped into the bioreactor and stabilized overnight before inoculation. Inoculum was prepared by growing cells for two days in spinners and then collected into 500 mL of fresh medium. The culture volume was 2.5 L in total, with an initial viable cell density of $1.5 \times 10^5$/mL. Cultures were grown for about 120 hours at three different inclination angles, 0°, 10° and 30° from the vertical. During the experiments, samples were removed to measure viable cell count and antibody production (Trypan-blue exclusion method was used for viable cell count and a sandwich type ELISA was used for antibody production). The results are shown in Table 1 and in FIGS. 3 and 4. In all three cases, the exponential growth and the maximum viable cell count were similar. The doubling in antibody production at 30° corresponded to a significantly longer stationary phase in cell growth, as summarized in Table 1.

TABLE 1

| Duration of stationary phase and antibody production | | | |
|---|---|---|---|
| Inclination | 0° | 10° | 30° |
| Stationary Phase (hours) | 25 | 38 | 45 |
| Antibody (mg/L) | 17 | 30 | 42 |

All publications mentioned in this specification are indicative of the level of skill of those skilled in the art to which this invention pertains. All publications are herein incorporated by reference to the same extent as if each individual publication was specifically and individually indicated to be incorporated by reference.

Although the foregoing invention has been described in some detail by way of illustration and example for purposes of clarity of understanding, it will be obvious that certain changes and modifications may be practised within the scope of the appended claims.

We claim:

1. A bioreactor for cultivating living cells in a liquid culture medium comprising:

a stationary vessel enclosing the cells and liquid culture medium, said vessel including oppositely spaced walls, said walls being inclined at an angle from the vertical so as to form an upper and a lower wall, said walls being tapered at their lower ends to form an apex; and means for introducing a circulating gas at the apex such that the liquid culture medium and the cells are lifted with the gas upwardly along the upper wall, the gas disengages from the liquid culture medium at the upper wall, and the liquid culture medium and the cells fall downwardly along the lower wall.

2. The bioreactor as set forth in claim 1, wherein the upper and lower walls are inclined at an angle between 10 and 45 degrees from the vertical and are substantially parallel.

3. The bioreactor as set forth in claim 2, wherein the vessel comprises a cylinder, which is tapered to form the apex at its lower end.

4. The bioreactor as set forth in claim 3, wherein the means for introducing gas comprises a gas sparger located at the apex and a pressurized source of gas.

5. The bioreactor as set forth in claim 2, wherein the upper and lower walls comprise parallel spaced plates, which plates converge at their lower end to form the apex.

6. The bioreactor as set forth in claim 5, wherein the means for introducing gas comprises a gas sparger located at the apex and a pressurized source of gas.

7. The bioreactor as set forth in claim 6, which further comprises a temperature control jacket around the vessel walls and means for introducing the liquid culture medium and the cells into the vessel.

8. The bioreactor as set forth in claim 7, which further comprises:
   means located at the upper end of the vessel for controlling moisture loss from the bioreactor; and
   means for venting gas from the top of the bioreactor.

9. A method of culturing living cells, comprising the steps of:
   (a) providing a vessel having oppositely spaced walls inclined at an angle to the vertical so as to form an upper and a lower wall, said walls being tapered at their lower ends to form an apex;
   (b) introducing a liquid culture medium and the cells to the vessel;
   (c) introducing a gas at the lower end of the walls at a rate sufficient to circulate the cells and liquid culture medium, such that the cells and the liquid culture medium are lifted with the gas upwardly along the upper wall, the gas disengages from the medium at the upper wall, and the cells and the liquid culture medium fall downwardly along the lower wall.

10. The method as set forth in claim 9, wherein the cells are shear sensitive cells and the gas includes oxygen so as to aerate the cells in addition to circulating.

11. The method as set forth in claim 10, wherein the cells are hybridoma cells.

12. The method as set forth in claim 9, wherein the upper and lower walls are substantially parallel.

13. The method as set forth in claim 12, wherein the vessel comprises a cylinder, which is tapered to form the apex at its lower end, and wherein the gas is introduced at the apex.

14. The method as set forth in claim 13, wherein the upper and lower walls are inclined at an angle between 10 and 45 degrees from the vertical.

15. The method as set forth in claim 12, wherein the vessel comprises spaced apart, substantially parallel plates, which plates converge to form the apex at their lower ends, and wherein the gas is introduced at the apex.

16. The method as set forth in claim 15, wherein the upper and lower walls are inclined at an angle between 10 and 45 degrees from the vertical.

* * * * *

UNITED STATES PATENT AND TRADEMARK OFFICE
CERTIFICATE OF CORRECTION

PATENT NO. : 5,443,985
DATED : August 22, 1995
INVENTOR(S) : George Z. LU et al.

It is certified that error appears in the above-indentified patent and that said Letters Patent is hereby corrected as shown below:

On the title page, item [73] Assignee:

line 3, delete "Alaska" and insert therefor --Alberta--.

Signed and Sealed this

Second Day of July, 1996

Attest:

BRUCE LEHMAN

Attesting Officer

Commissioner of Patents and Trademarks